June 27, 1972 H. A. RASCHKE Re. 27,408

CLAMP-ON PROTECTIVE HOOD

Original Filed Nov. 3, 1966

INVENTOR.
HERBERT A. RASCHKE

BY

Townsend and Townsend

ATTORNEYS

United States Patent Office

Re. 27,408
Reissued June 27, 1972

27,408
CLAMP-ON PROTECTIVE HOOD

Herbert A. Raschke, Greenbrae, Calif., assignor to E. D. Bullard Company, Sausalito, Calif.

Original No. 3,427,660, dated Feb. 18, 1969, Ser. No. 591,791, Nov. 3, 1966. Application for reissue Dec. 17, 1969, Ser. No. 888,181
Int. Cl. A61f *9/00;* A62b *7/00*
U.S. Cl. 2—10 11 Claims

Matter enclosed in heavy brackets [ ] appears in the original patent but forms no part of this reissue specification; matter printed in italics indicates the additions made by reissue.

ABSTRACT OF THE DISCLOSURE

A hood attachable to the periphery of the periphery of the rim of a hard safety hat, which hood extends down over the face, neck and shoulders of the wearer to form a protective atmosphere around the wearer's head. A structure for quickly attaching and detaching the hood to the safety hat which structure assures an air tight seal between the hood and the hat to exclude deleterious airborne substances from interior of the hood. An improved system for conveying and distributing air to the interior of the hood.

This invention relates to a protective hood of the type used by sandblasters and the like, which hood includes provisions for clamping the same onto a conventional safety hat or hard hat.

In certain hazardous occupations such as sandblasting and acid handling, it is typical that persons engaging in such occupations wear a protective hood that covers the head, face, neck and shoulders of such person. Prior art structures of unitary form for this purpose have been available and have served their intended function well. Persons engaged in such hazardous occupations as mentioned above are required to devote substantial portions of their time to relatively non-hazardous activities in which the necessity for complete head and face protection is not present. Safety practices, however, require that the top of the wearer's head be protected by a conventional safety hat or hard hat at all times, and such requirement has necessitated that the person engaged in hazardous occupations of the type mentioned above, be provided with a protective hood and a safety or hard hat for alternate use. Such practice has increased the amount of equipment needed for the safe performance of the hazardous occupations and additionally, affords a temptation for the person to fail to don a safety hat when the protective hood is removed; such as, for example, when the safety hat is at a location remote from the location where the protective hood is removed.

It is an object of this invention therefore, to provide a protective hood that is adapted to clamp on to a conventional hard hat or safety helmet so that the helmet and hood can be used together or the helmet can be used alone. By accomplishing this object the present invention renders much more convenient adherence to safety requirements under all conditions.

A feature and advantage of the invention is that the amount and weight of equipment required by a given workman are reduced so that not only is the workman less fatigued from carrying equipment to and from the job, but he is more likely to have the equipment available for use at all times.

In accomplishing the objects of the invention, it is important that the structure for attaching the hood to the helmet be quick and simply operable, and that it affords an impervious joint between the hood and the helmet.

In the present invention such is accomplished by providing a U-shaped band, such as an aluminum extrusion which is formed to totally circumscribe the rim of the helmet. Such extrusion is totally encased in a hem formed at the upper extremity of the hood and the free ends of the extrusion are provided with a mechanism for drawing such free ends together. Thus, when the U-shaped extrusion is mounted onto the rim of the hat in embracing relation thereto, and the tensioning mechanism is engaged, the force of the tension in the extrusion intimately draws the flexible hood material into contact with the hat rim to form an impervious joint therebetween.

A further object of this invention is to provide an improved air supply system for hoods of the type referred to above. Because the hoods so completely surround and enclose the head, face and neck of the wearer, it is typical to have a forced air supply in such hoods. In the present invention the air is supplied to the hood adjacent the joint between the hood and the helmet, that is, closely adjacent and above the face of the wearer. The air supply distributing system of the invention includes a hollow tube removably secured around the hood which tube is provided with a plurality of apertures or jet openings for distributing the air adjacent the respiratory organs of the user. Because the tube is necessarily relatively small (for example, a ⅜ inch I.D. vinyl tube) the air velocity through the tube and through the jet openings must be made sufficiently high to deliver the required amount of air that a substantial hissing noise is produced. Such noise is not only uncomfortable for the wearer of the apparatus, but it is dangerous in that it frequently muffles exterior noises which would otherwise warn the user that danger is impending. The present invention provides an improved air distributor system that includes a knitted fabric sleeve mounted over the above-mentioned apertured tube, the nature of the knitted sleeve being such that it is porous with respect to the air issuing from the tube openings, but at the same time, distributes the air more uniformly and breaks up sound producing jets of air.

The air supply system provided by the present invention because it is at all times encased within the hood has a longevity greater than that of the hood itself. Therefore, it is a further object of the invention to provide an air supply system which is readily and conveniently removable from the hood in the event of replacement of the hood.

Other objects, features and advantages of the present invention will be more apparent after referring to the following specification and accompanying drawing in which.

Figure 1:
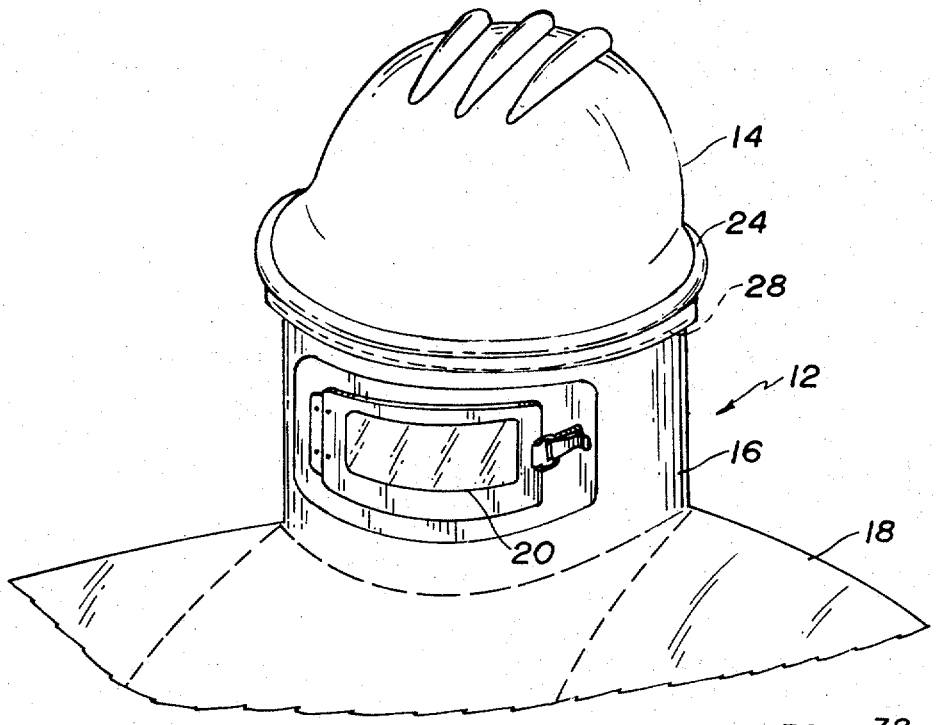
FIG. 1 is a perspective view of a hood of the present invention mounted on a safety helmet.
Figure 3:
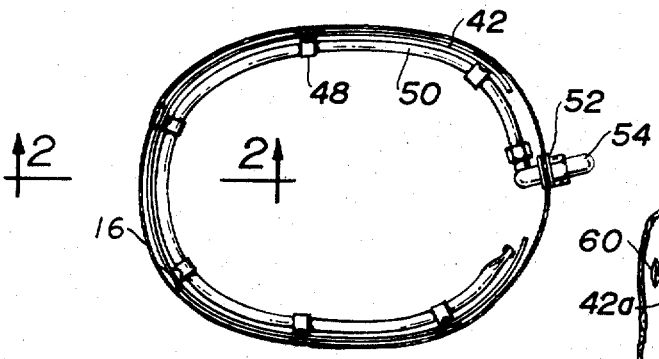
FIG. 3 is a top view in cross section of the air distributing apparatus of the present invention, said view being taken generally along line 3—3 of FIG. 2.
Figure 2:
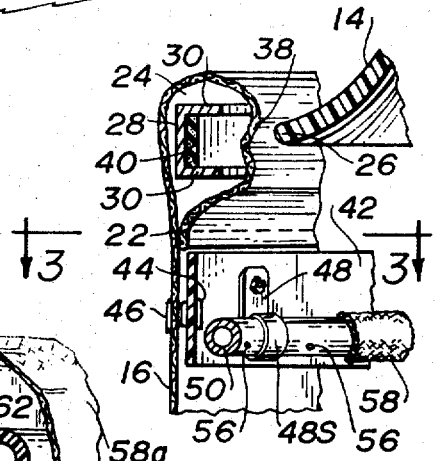
FIG. 2 is a fragmentary cross-sectional view in elevation showing in detail the mechanism for securing the hood to the helmet rim.

Referring more particularly to the drawing, reference numeral 12 indicates a hood of the present invention shown in FIGURE 1 attached to a hard hat 14 of more or less conventional form. Hood 12 is constructed of any suitable flexible material that is impervious to environmental conditions; exemplary materials are neoprene leather, vinyl, neoprene impregnated fabric, etc. Hood 12 includes a generally cylindric face and head protect- ıg portion 16 from the lower edge of which depends a ıoulder and trunk protective portion 18. A transparent ıce plate 20 is included in cylindric portion 16 at eye vel. The upper extremity of face protective portion 16 stitched or similarly secured back onto itself at 22 to ɜfine hem opening 24. The diameter of the cylinder ɔrmed by face protective portion 16 is such that the ɔper opening is approximately congruent to the rim of at 14, such rim being indicated at 26 in FIGURE 2.

Figure 4:
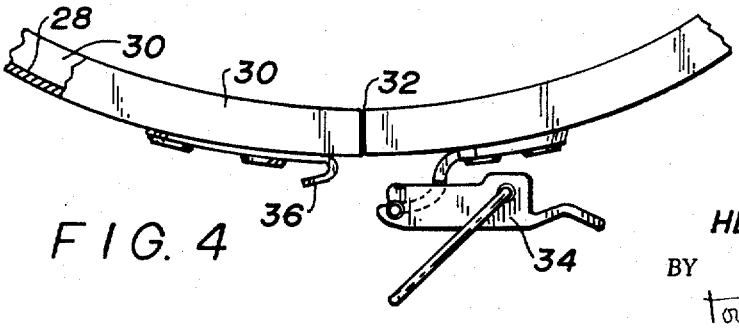
FIG. 4 is a fragmentary top view of the latching device for securing the hood to the safety helmet.

Disposed within the hem opening 24, is a substantially gid U-shaped ring 28 which includes parallel spaced ɔart legs 30 which are spaced apart sufficiently to emrace rim 26. Ring 28 is split as indicated at 32 in FIGRE 4, which split together with the small degree of ɜilience or bendability permits the ring to be expanded ıfficiently that the ring can be engaged onto hat rim 26. fter such engagement a toggle lever 34 affixed to ring 28 ɔ one side of split 32, is engaged with a toggle hook 36, ffixed to ring 28 on the other side of split 32. Operation f toggle lever 34 draws the ends of ring 28 together to ıe position shown in FIGURE 4 so that the ring 28 is ıgaged with hat rim 26 and relative movement between ıe two is inhibited by flanges 30. Compressed between hat m 26 and U-shaped ring 28 is a portion 38 of the marial that defines hem opening 24. Such compression of ıe material assists in providing an impervious joint beveen the hood and hat 14. A perfect joint can be assured y the provision of a gasket 40, of sponge rubber or the ke located between flanges 30. From the foregoing it is ear that the wearer of a safety hat can quickly attach ıe hood of this invention to such safety hat by disengagıg toggle lever 34, fitting the hood over rim 26 so that ıe rim is between flanges 30, and by reengaging toggle ver 34 with toggle hook 36. The installation of the hood ıto the safety hat and the removal of the hood from ıe safety hat can be performed quickly, thus encouragg the use of the hood at all times dictated by safety quirements.

The ambient atmosphere in which the apparatus is pically employed is normally so contaminated so as to ɜnder it unfit for breathing. Thus it is conventional to ıpply air from some external source. The present invenon provides mechanisms for conveniently conveying and stributing the air within the hood. Supported within ıe hood immediately below the line of stitching 22 is a ɜxible band 42 which is adapted for removable mountg within the hood. For the latter purpose, band 42 is ɔvided with a plurality of snap fastener elements 44, ıe hood having a corresponding number of complementa- snap fastener members 46 mounted therein. A plurality clamp members 48 is secured around the inner surface band 42, each clamp member including a looped segent 48s for supporting a hollow tube 50. At the rear of ıe hood a fitting 52 is provided for conducting tube 50 ırough hood portion 16, the exterior of the tube being lapted at 54 for coupling to an air hose or like fresh r source. Within hood 12 tube 50 is provided with a urality of downwardly inwardly directed holes or jet ɔenings 56 for distributing the air entering through tube ). In order to properly distribute the air through jet ɔenings 56, each opening must be of relatively small ameter compared with the inside diameter of tube 50, a consequence of which the air issuing through the t openings causes a hissing noise which is both disturbg to the wearer of the apparatus and hazardous, since ɜternal sounds are rendered inaudible.

To obviate the aforementioned condition the present vention provides a knitted tube or sleeve 58 which fits ver the tube 50. Sleeve 58 breaks up and distributes the r issuing from jet openings 56 so as to substantially iminate creation of any annoying sound.

Figure 5:
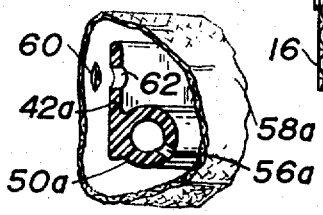
FIG. 5 is a fragmentary view in cross-section showing an improved form of air distributor tube in accordance with the present invention.

An alternate form of the air distribution tube is shown ı FIGURE 5 and includes an air conduit 50a with which integrally molded a mounting band 42a. A fabric sleeve 8a of greater inside diameter than sleeve 58 is mounted in circumscribing relation to both conduit 50a and strip 42a and performs the same function of muffling air flow from jet openings 56a. The sleeve is slit as at 60 to correspond with holes 62 in strip 42a for permitting removable attachment of the modified air tube within the hood by insertion of snap fastener members 44 through the aligned slits and holes.

It will be seen that the air distributing system of the present invention is removable from the hood, an important economic advantage because the air tube normally has a greater longevity than the hood itself which is subjected to abrasion from the contaminate materials of the atmosphere in which the hood is used.

Moreover, the present invention provides a hood that can be readily installed onto and removed from a conventional safety hat to the end that the user thereof is at all times properly equipped for compliance with safety requirements. Additionally the hood is provided with an efficient air supply system which assures the user thereof an adequate air supply without annoying hissing sounds.

Although one embodiment of the present invention has been shown and described it will be obvious that other adaptations and modifications can be made without departing from the true spirit and scope of the invention.

What is claimed is:

1. A hood for protectively enclosing the face, neck and shoulders of the wearer of a rimmed hard safety hat comprising: a flexible impervious shroud having an upper opening substantially congruent to the rim of said safety hat and formed to hang down to cover the face, neck and shoulders of the wearer, said shroud being formed with a front opening adjacent the eyes of the wearer, a transparent sheet spanning said front opening in sealed relation to said shroud, and means engageable with the rim for releasably securing said shroud around the rim of said hat in air tight relation thereto so as to preclude entrance of airborne contaminants between said hat and said shroud when said releasable securing means is secured to the hat rim, said securing means having a hem defining a tubular enclosure around the upper opening of said shroud, bendable band member U-shaped in cross-section and having end portions disposed in said enclosure, said enclosure being formed so that a layer of said shroud is positioned between said U-shaped member and said hat rim, and means for drawing the end portions of said U-shaped member together to retain said U-shaped member in encircling contacting relation with the rim of the safety hat and to compress the shroud into sealing relation around the hat rim.

2. The invention of claim 1 including a resilient gasket secured to the bottom of said U-shaped member and adapted to be compressed when the U-shaped member is engaged around the rim of the hat, said gasket acting to urge the material of which the shroud is made into intimate continuous engagement with the said rim.

3. The invention of claim 1 wherein said band attaching means comprises: a toggle lever mounted on one end portion of said band and a hook engageable by said toggle member on the other end portion of said band.

4. The invention of claim 1 in combination with an air tube circumscribing said shroud adjacent said upper opening, said air tube being perforated about the periphery thereof to permit egress of air into said shroud, and means for conducting said air tube through said shroud for affording connection to said air tube of an air supply exterior of said shroud.

5. The invention of claim 4 including a knitted fabric sleeve circumscribing said air tube for distributing air issuing from the openings in said tube and for reducing the noise level of the air.

6. The invention of claim 4 including means for removably securing said air tube in said shroud.

7. The invention of claim 6 wherein said removably securing means comprises a mounting band secured to said tube, a plurality of first snap fastener members affixed to said mounting band, an equal plurality of second snap fastener members affixed to said shroud subjacent the upper opening of said shroud, said first snap members being removably engageable with said second snap members.

8. The invention of claim 7 wherein said mounting band and said tube are integrally formed in a unitary structure.

*9. A head protective enclosure including a rigid hood member for protecting the top of the wearer's head and a shroud that depends from the rigid hood member in air tight relation thereto for enclosing the wearer's face, neck, and shoulders, a perforate air tube mounted within the enclosure with said perforations in said tube substantially circumscribing the wearer's head for distributing air through said perforations to the wearer of the enclosure, and a knitted fabric sleeve circumscribing said air tube for the full extent of said perforations for distributing air issuing from the perforations in said tube and for reducing the noise level of the air.*

*10. The invention of claim 9 in combination with means for releasably securing said shroud to said rigid member.*

*11. The invention of claim 10 including means for securing said air tube to said shroud.*

References Cited

The following references, cited by the Examiner, are of record in the patented file of this patent or the original patent.

UNITED STATES PATENTS

| | | | |
|---|---|---|---|
| 504,880 | 9/1893 | Konig | 128—142.7 |
| 1,872,877 | 8/1932 | Bowers | 128—142.3 |
| 2,296,338 | 9/1942 | Dakin | 128—142.3 |
| 2,410,593 | 11/1946 | Wright | 128—142.3 |
| 2,577,607 | 12/1951 | Conley | 128—142.3 |
| 2,896,617 | 7/1959 | Gibbons | 128—142.7 X |
| 3,114,914 | 12/1963 | Ruggiero | 2—8 |
| 3,310,811 | 3/1967 | Iacono | 2—6 |
| 2,882,894 | 4/1959 | Fashey et al. | 128—141 |

H. HAMPTON HUNTER, Primary Examiner

U.S. Cl. X.R.

2—4; 128—142.5, 142.7